US006929632B2

(12) United States Patent
Nita et al.

(10) Patent No.: US 6,929,632 B2
(45) Date of Patent: Aug. 16, 2005

(54) ULTRASONIC DEVICES AND METHODS FOR ABLATING AND REMOVING OBSTRUCTIVE MATTER FROM ANATOMICAL PASSAGEWAYS AND BLOOD VESSELS

(75) Inventors: Henry Nita, Mission Vieyo, CA (US); Timothy C. Mills, Corona Del Mar, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 190 days.

(21) Appl. No.: 10/185,397

(22) Filed: Jun. 27, 2002

(65) Prior Publication Data

US 2003/0009125 A1 Jan. 9, 2003

Related U.S. Application Data

(60) Division of application No. 09/388,794, filed on Sep. 2, 1999, now Pat. No. 6,454,757, which is a division of application No. 08/815,673, filed on Mar. 12, 1997, now Pat. No. 5,957,882, which is a continuation of application No. 08/222,999, filed on Apr. 5, 1994, now abandoned, and a continuation-in-part of application No. 07/640,190, filed on Jan. 11, 1991, now Pat. No. 5,304,115.

(51) Int. Cl.$^7$ .............................................. A61M 31/00
(52) U.S. Cl. ...................... 604/508; 604/22; 606/169; 606/41
(58) Field of Search ........................... 604/508, 21, 22, 604/517, 500, 515, 73, 113, 523, 2; 606/49, 41, 28, 31, 159, 193, 169–171

(56) References Cited

U.S. PATENT DOCUMENTS

| 3,352,303 A | 11/1967 | Delaney |
| 3,433,226 A | 3/1969 | Boyd |
| 3,526,219 A | 9/1970 | Balamuth |
| 3,565,062 A | * 2/1971 | Kuris .......................... 606/169 |
| 3,589,363 A | 6/1971 | Banko |
| 3,618,594 A | 11/1971 | Banko |
| 3,809,093 A | 5/1974 | Abraham |
| 3,823,717 A | 7/1974 | Pohlman |
| 3,861,391 A | 1/1975 | Antonevich et al. |
| 3,896,811 A | 7/1975 | Storz |
| 4,188,952 A | 2/1980 | Loschilov et al. |

(Continued)

FOREIGN PATENT DOCUMENTS

| DE | 2349120 | 4/1975 |
| DE | 2438648 | 2/1976 |
| DE | 2453058 | 5/1976 |
| DE | 2453126 | 5/1976 |
| DE | 2541919 | 3/1977 |
| DE | 2703486 | 12/1977 |
| DE | 8119209 | 10/1981 |
| DE | 3707921 A1 | 3/1986 |
| DE | 3726210 | 8/1987 |
| DE | 3707567 | 9/1987 |

(Continued)

OTHER PUBLICATIONS

Circulation, vol. 81, No. 2, Feb. 1990, "Application of a New Phased–Array Ultrasound Imaging Catheter in the Assessment of Vascular Dimensions," pp. 660–666.

"Ultrasonic Energy Causes Doe–Dependent, Endothelium–Independent Arterial Relaxation"–T. Fischell, et al. Abstracts of the 63rd Scientific Sessions, pp. 111–219.

*Primary Examiner*—Cris L. Rodriguez
(74) *Attorney, Agent, or Firm*—Fulwider Patton Lee & Utecht, LLP

(57) ABSTRACT

Disclosed are methods and devices for removing obstructive matter from anatomical passageways, including the removal of obstructive matter from the cerebral vasculature, prostatic obstructions from the urinary tract and/or obstructive matter from the fallopian tubes.

10 Claims, 3 Drawing Sheets

U.S. PATENT DOCUMENTS

| | | | |
|---|---|---|---|
| 4,214,586 A | 7/1980 | Mericle | |
| 4,223,676 A | 9/1980 | Wuchinich et al. | |
| 4,337,090 A | 6/1982 | Harrison | |
| 4,366,819 A | 1/1983 | Kaster | |
| 4,431,006 A | 2/1984 | Trimmer et al. | |
| 4,474,180 A | 10/1984 | Angulo | |
| 4,505,767 A | 3/1985 | Quin | |
| 4,565,589 A | 1/1986 | Harrison | |
| 4,587,958 A | 5/1986 | Noguchi et al. | |
| 4,587,972 A | 5/1986 | Morantte | |
| 4,589,419 A | 5/1986 | Laughlin et al. | |
| 4,665,906 A | 5/1987 | Jervis | |
| 4,692,139 A * | 9/1987 | Stiles | 604/22 |
| 4,698,058 A * | 10/1987 | Greenfeld et al. | 604/266 |
| 4,741,731 A | 5/1988 | Starck | |
| 4,748,971 A | 6/1988 | Borodulin et al. | |
| 4,750,488 A * | 6/1988 | Wuchinich et al. | 606/128 |
| 4,750,902 A | 6/1988 | Wuchinich et al. | |
| 4,764,165 A | 8/1988 | Reimels | |
| 4,765,332 A * | 8/1988 | Fischell et al. | 606/159 |
| 4,794,931 A | 1/1989 | Yock | |
| 4,799,496 A | 1/1989 | Hargraves | |
| 4,800,876 A | 1/1989 | Fox et al. | |
| 4,808,153 A | 2/1989 | Parisi | |
| 4,811,743 A | 3/1989 | Stevens | |
| 4,821,731 A | 4/1989 | Martinelli | |
| 4,841,977 A | 6/1989 | Griffith | |
| 4,844,092 A | 7/1989 | Rydell | |
| 4,867,141 A * | 9/1989 | Nakada et al. | 601/4 |
| 4,870,953 A | 10/1989 | DonMichael | |
| 4,886,061 A * | 12/1989 | Fischell et al. | 606/159 |
| 4,898,575 A | 2/1990 | Fischell et al. | |
| 4,917,097 A | 4/1990 | Proudian et al. | |
| 4,919,133 A | 4/1990 | Chiang | |
| 4,920,954 A | 5/1990 | Alliger et al. | |
| 4,923,441 A | 5/1990 | Shuler | |
| 4,924,863 A | 5/1990 | Sterzer | |
| 4,936,281 A | 6/1990 | Stasz | |
| 4,957,111 A | 9/1990 | Millar | |
| 4,960,411 A | 10/1990 | Buchbinder | |
| 4,966,583 A | 10/1990 | Debbas | |
| 4,967,653 A | 11/1990 | Hinz | |
| 4,967,753 A | 11/1990 | Haase et al. | |
| 4,979,939 A | 12/1990 | Shiber | |
| 4,988,356 A | 1/1991 | Crittenden | |
| 4,989,583 A | 2/1991 | Hood | |
| 5,058,570 A | 10/1991 | Idemoto et al. | |
| 5,061,238 A | 10/1991 | Shuler | |
| 5,069,664 A | 12/1991 | Guess et al. | |
| 5,076,276 A | 12/1991 | Sakurai et al. | |
| 5,100,423 A | 3/1992 | Fearnot | |
| 5,151,085 A | 9/1992 | Sakurai | |
| 5,163,421 A | 11/1992 | Bernstein | |
| 5,188,589 A | 2/1993 | Wypych | |
| 5,199,943 A | 4/1993 | Wypych | |
| 5,209,719 A * | 5/1993 | Baruch et al. | 604/22 |
| 5,211,625 A | 5/1993 | Sakurai | |
| 5,242,385 A | 9/1993 | Strukel | |
| 5,248,296 A | 9/1993 | Alliger | |
| 5,255,669 A | 10/1993 | Kubota | |
| 5,261,877 A | 11/1993 | Fine | |
| 5,269,297 A | 12/1993 | Weng | |
| 5,312,328 A | 5/1994 | Nita | |

FOREIGN PATENT DOCUMENTS

| | | |
|---|---|---|
| DE | 3707921 | 9/1987 |
| DE | 3826414 | 2/1989 |
| DE | 3812836 | 4/1990 |
| DE | 4114826 | 5/1991 |
| EP | 189329 | 7/1986 |
| EP | 293472 | 11/1986 |
| EP | 0 208 175 | 1/1987 |
| EP | 208175 | 1/1987 |
| EP | 0209468 | 1/1987 |
| EP | 234951 | 2/1987 |
| EP | 0424231 | 4/1989 |
| EP | 0 316 796 | 5/1989 |
| EP | 347098 | 6/1989 |
| EP | 315290 | 10/1989 |
| EP | 443256 | 12/1990 |
| EP | 472368 | 2/1992 |
| FR | 2424733 | 11/1980 |
| FR | 2 641 693 | 7/1990 |
| FR | 2641693 | 7/1990 |
| FR | 2 643 272 | 8/1990 |
| FR | 2643272 | 8/1990 |
| GB | 1520448 | 8/1978 |
| GB | 1531659 | 11/1978 |
| GB | 2208138 A | 3/1989 |
| GB | 2212267 | 7/1989 |
| WO | WO 87/01276 | 3/1987 |
| WO | WO 87/05793 | 10/1987 |
| WO | WO 89/05123 | 6/1989 |
| WO | WO 89/06515 | 7/1989 |
| WO | WO 89/07419 | 8/1989 |
| WO | WO 90/01300 | 2/1990 |
| WO | WO 90/07303 | 7/1990 |
| WO | WO 91/02489 | 3/1991 |
| WO | WO 91/14401 | 10/1991 |
| WO | WO 92/10140 | 6/1992 |
| WO | WO 92/11815 | 7/1992 |
| WO | WO 92/15253 | 9/1992 |

* cited by examiner

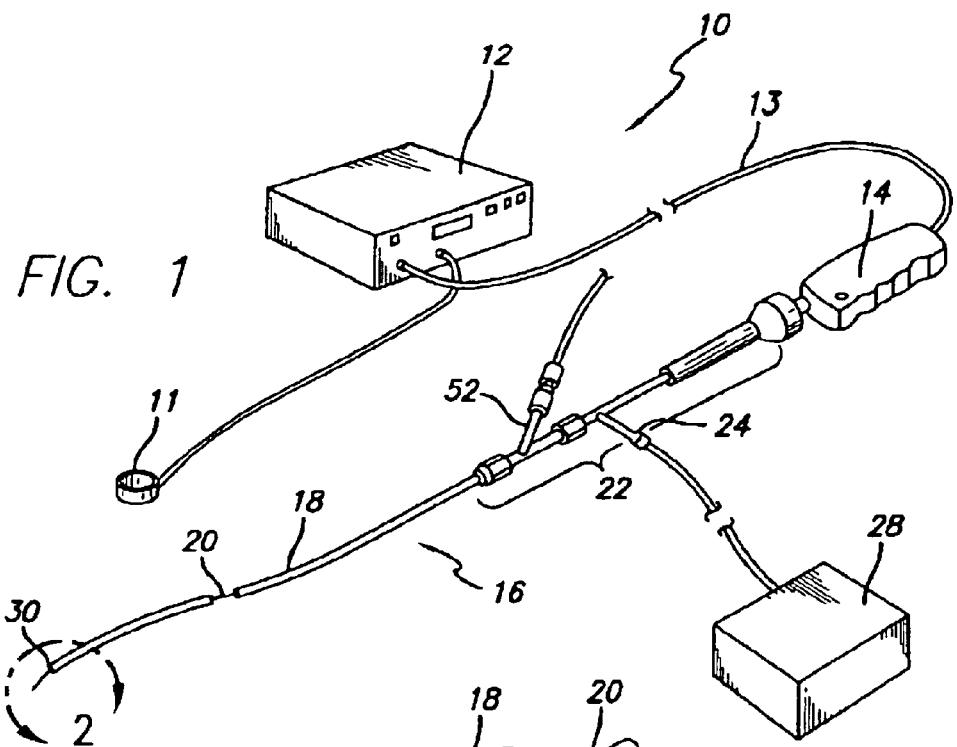
FIG. 1
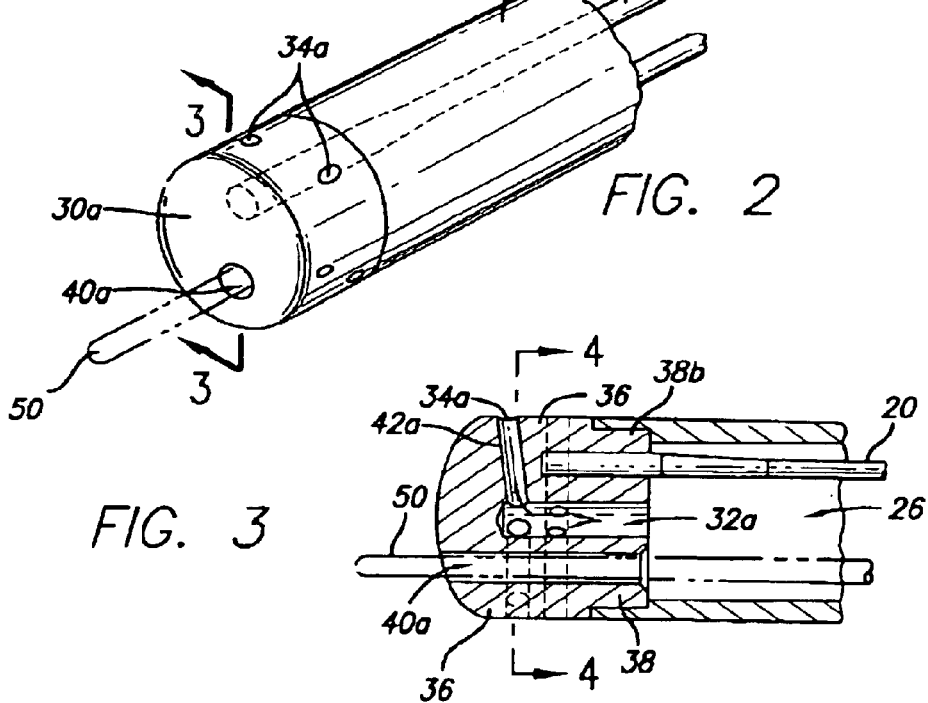
FIG. 2
FIG. 3

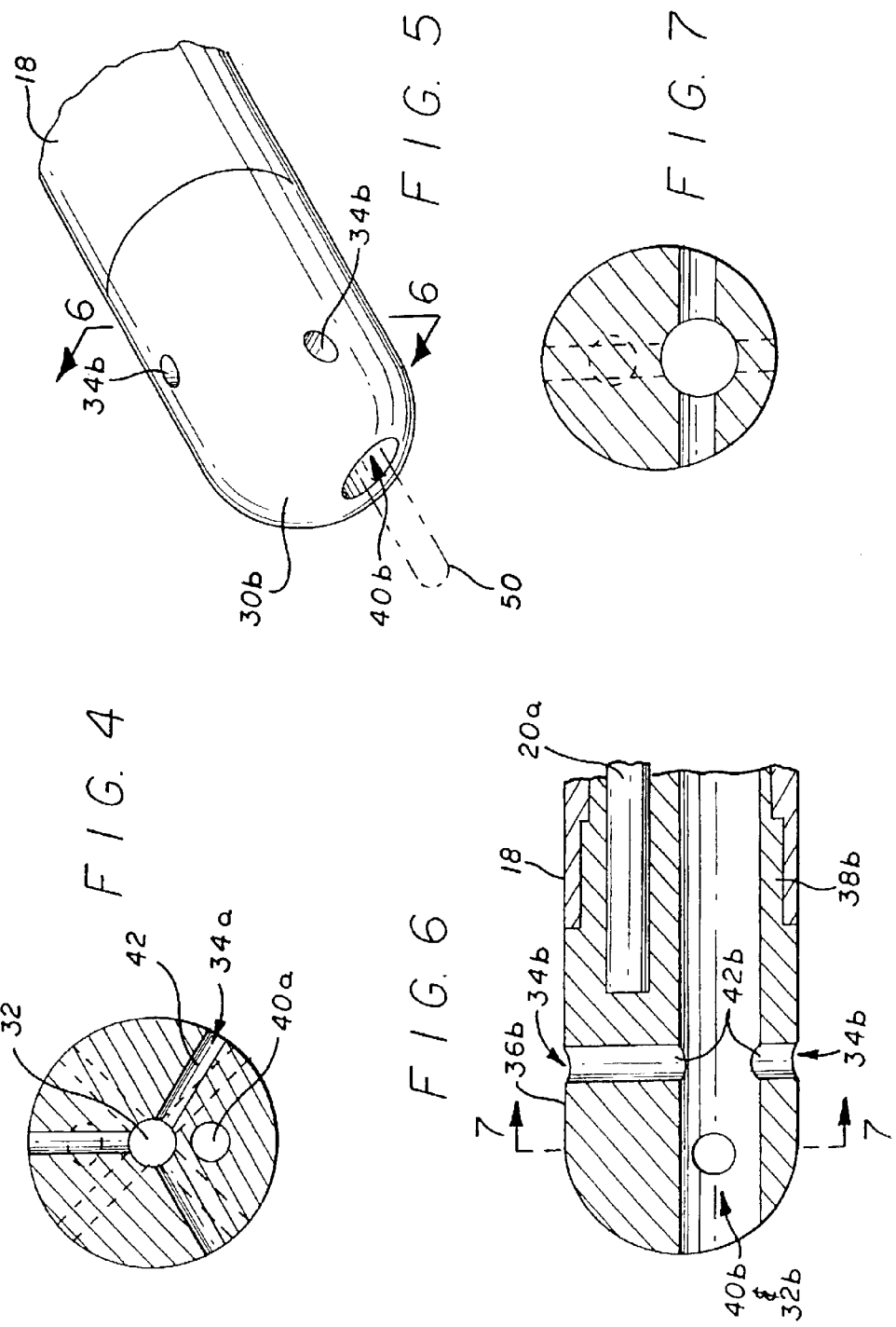

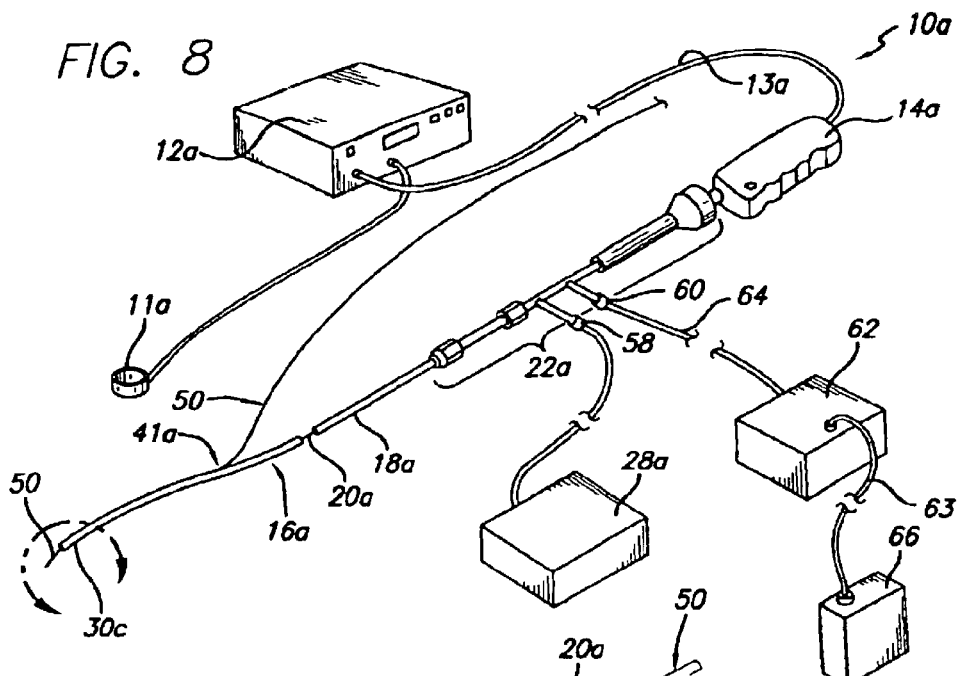
FIG. 8
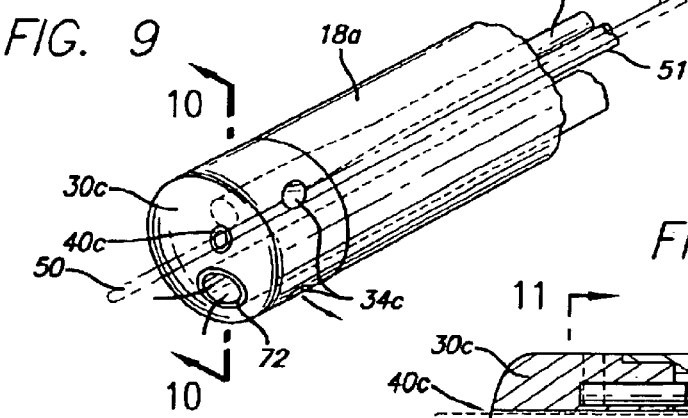
FIG. 9
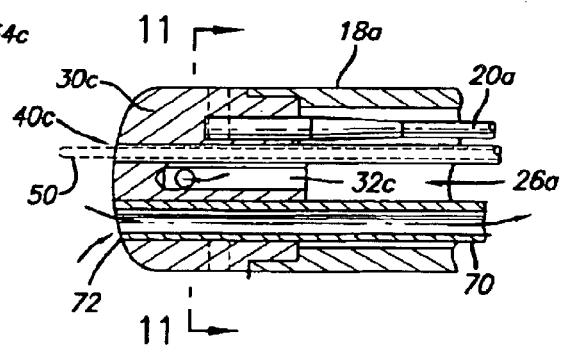
FIG. 10
FIG. 11

ULTRASONIC DEVICES AND METHODS FOR ABLATING AND REMOVING OBSTRUCTIVE MATTER FROM ANATOMICAL PASSAGEWAYS AND BLOOD VESSELS

RELATED APPLICATION AND INCORPORATION BY REFERENCE

This patent application is a divisional of U.S. patent application Ser. No. 09/388,794, filed Sep. 2, 1999, which is now U.S. Pat. No. 6,454,757, which is a divisional of U.S. patent application Ser. No. 08/815,673 filed Mar. 12, 1997, which is now U.S. Pat. No. 5,957,882, which is a continuation of U.S. patent application Ser. No. 08/222,999 filed Apr. 5, 1994, now abandoned, and is a continuation-in-part of U.S. patent application Ser. No. 07/640,190 filed Jan. 11, 1991, which is now U.S. Pat. No. 5,304,115, and the entirety of each is expressly incorporated herein by reference.

Also, applicant expressly incorporates herein by reference the entirety of U.S. Pat. No. 5,267,954 entitled ULTRASOUND CATHETER FOR REMOVING OBSTRUCTIONS FROM TUBULAR ANATOMICAL STRUCTURES SUCH AS BLOOD VESSELS, issued Dec. 7, 1993.

FIELD OF THE INVENTION

The present invention pertains generally to medical equipment and, more particularly, to ultrasonic devices and methods for removing obstructive matter from anatomical passageways, including the removal of obstructive matter from the cerebral vasculature, prostate tissue from the urinary tract and/or obstructive matter from the fallopian tubes.

BACKGROUND OF THE INVENTION

The prior art has included various ultrasonically vibrated surgical and ablative instruments for treating obstructive disorders of blood vessels and other anatomical passageways or cavities.

The prior art devices which, purportedly utilize ultrasonic energy, alone or in conjunction with other treatment modalities, to treat obstructions within blood vessels or other anatomical structures of the body include those described in U.S. Pat. No. 3,433,226 (Boyd), U.S. Pat. No. 3,823,717 (Pohlman, et al.), U.S. Pat. No. 4,808,153 (Parisi), U.S. Pat. No. 4,936,281 (Stasz), U.S. Pat. No. 3,565,062 (Kuris), U.S. Pat. No. 4,924,863 (Sterzer), U.S. Pat. No. 4,870,953 (Don Michael, et al.), U.S. Pat. No. 4,920,954 (Alliger, et al.), and U.S. Pat. No. 5,100,423 (Fearnot), U.S. Pat. No. 4,136,700 (Broadwin), U.S. Pat. No. 4,192,294 (Vasilevsky), U.S. Pat. No. 4,750,448 (Wuchinich), U.S. Pat. No. 4,750,902 (Wuchinich), U.S. Pat. No. 4,765,332 (Fischell), U.S. Pat. No. 4,808,153 (Parisi), U.S. Pat. No. 4,832,023 (Murphy-Chutorian), U.S. Pat. No. 4,867,141 (Nakada), U.S. Pat. No. 4,870,953 (Don Michael), U.S. Pat. No. 4,877,033 (Seitz), U.S. Pat. No. 4,886,061 (Fischell), U.S. Pat. No. 4,922,902 (Wuchinich), U.S. Pat. No. 4,936,281 (Stasz), U.S. Pat. No. 4,974,581 (Wiksell), U.S. Pat. No. 4,989,588 (Kubota), U.S. Pat. No. 5,058,570 (Idemoto), U.S. Pat. No. 5,069,664 (Guess), U.S. Pat. No. 5,149,319 (Unger), U.S. Pat. No. 5,151,084 (Khek), U.S. Pat. No. 5,154,723 (Kubota), U.S. Pat. No. 5,156,143 (Bocquett), U.S. Pat. No. 5,163,421 (Bernstein), U.S. Pat. No. 5,163,433 (Kagawa), as well as foreign publications nos. WO87-05739 (Cooper), WO89-06515 (Bernstein, et al.), WO90-0130 (Sonic Needle Corp.), EP316789 (Don Michael, et al.), DE3,821,836 (Schubert), DE2,438,648 (Pohlman), GB 1,531,659 (Gekhman, et al.), EP 342448 (Bakelite), EP 293472 (Bakelite), and EP 209468 (Sarl).

Although the prior art has included numerous devices for ultrasonic treatment of intracorporeal obstructions, there remains a need in the art for the development of new and improved ultrasonic devices having improved or differing capabilities for specific blood vessels or regions of the body, such as the intracranial and extracranial vessels of the cerebral vasculature and/or the tubes and ducts of the genitourinary tracts of the male and female.

SUMMARY OF THE INVENTION

The present invention provides methods for ultrasonically treating obstructions of anatomical passageways of the mammalian body with concomitant infusion of a fluid (e.g., saline solution) in a manner which will dilate or fluidically expand the surrounding anatomical structure so as to facilitate passage of a catheter through the obstructed region of the anatomical structure. Methodologies in accordance with this embodiment of the invention are particularly useful in treating intravascular obstructions as well as obstructions of the male or female urogenital tract, including, but not limited to obstructions of the fallopian tubes and prostatic obstructions of the male urethra.

Further in accordance with the invention, there are provided methods for ultrasonically treating obstructions within anatomical passageways of the mammalian body while concomitantly aspirating and removing matter from the anatomical passageway so as to prevent escape of solid particles or other matter created or released by the ultrasonic treatment process In accordance with this embodiment of the invention, there are provided methodologies which are particularly applicable in the ultrasonic treatment of obstructions within intracranial and extracranial cerebral blood vessels which supply blood to the mammalian brain.

Further in accordance with the invention, there is provided a first embodiment of an ultrasound treatment system incorporating an ultrasound delivery catheter having one or more fluid infusion lumens for infusing fluid through the catheter, to effect fluidic dilation of the anatomical structure wherein the obstruction is located.

Still further in accordance with the invention, there is provided a second embodiment of an ultrasound treatment system incorporating an ultrasound delivery catheter having at least one aspiration lumen extending longitudinally through the catheter to aspirate and remove particles or other debris from the anatomical structure wherein the obstruction is located.

Further objects and advantages of the invention will become apparent to those skilled in the art upon reading and understanding the following detailed description and the accompanying drawings.

BRIEF DESCRIPTION OF THE DRAWINGS

FIG. 1 is a perspective view of a first embodiment of an ultrasonic system of the present invention for removing obstructions from genitourinary pathways or other anatomical structures of the body.

FIG. 2 is an enlarged perspective view of a first embodiment of a distal catheter tip which may be incorporated in the system of FIG. 1.

FIG. 3 is a longitudinal sectional view through line 3—3 of FIG. 2.

FIG. 4 is a cross-sectional view through line 4—4 of FIG. 3.

FIG. 5 is an enlarged perspective view of a second embodiment of a catheter tip which may be incorporated into the ultrasound system of FIG. 1.

FIG. 6 is a longitudinal sectional view through line 6—6 of FIG. 5.

FIG. 7 is a cross-sectional view through line 7—7 of FIG. 6.

FIG. 8 is a perspective view of a second embodiment of an ultrasound treatment system of the present invention.

FIG. 9 is an enlarged perspective view of a distal catheter tip which may be incorporated into the ultrasound system of FIG. 8.

FIG. 10 is a longitudinal sectional view through line 10—10 of FIG. 9.

FIG. 11 is a cross-sectional view through line 11—11 of FIG. 10.

DETAILED DESCRIPTION OF THE PREFERRED EMBODIMENTS

The following detailed description and the accompanying are provided for purposes of describing and illustrating presently preferred embodiments of the invention and are not intended to cover every possible embodiment or configuration of the invention, nor are they intended to limit the scope of the accompanying claims in any way.

With references to the drawings, FIGS. 1–7 are directed to a first embodiment of the invention preferably useable to dilate and treat obstructive disorders of various anatomical passageways, including the urethra and/or fallopian tubes. FIGS. 8–11 are directed to a second embodiment of the invention preferably useable to effect a) ultrasonic ablation of obstructive matter and b) aspiration of the reduced or morseled matter from the treatment site, such as a cerebral blood vessel or other passageway of the body wherein prompt aspiration or removal of any solid matter is desired.

i. Elements and Components of the First Embodiment

A first embodiment of an ultrasound treatment system 10 of the present invention, shown in FIG. 1, comprises an electrical signal generator 12 (e.g., Model UAG-1110, Baxter Healthcare Corporation, Cardiovascular Group, Interventional Cardiology Division, Irvine, Calif.) connected by way of cable 13 to an ultrasound transducer 14 (e.g., Model UAT-1000, Baxter Healthcare Corporation, Irvine, Calif.) operable to convert the electrical signal from the signal generator 12, into ultrasonic vibration. An elongate ultrasound catheter 16 is coupled to the ultrasound transducer 14 to transmit ultrasonic vibration from the transducer 14 to a desired treatment location adjacent the distal end of the catheter 16.

The catheter 16 component of the first embodiment of the ultrasound treatment system 10 may comprise an elongate flexible catheter body 18 formed of pliable material and an elongate ultrasound transmission wire or member 20 which extends longitudinally through the catheter body 18. The ultrasound transmission wire or member 20 extends proximally through a proximal connector assembly 22 whereby the proximal end of the ultrasound transmission member 20 may be coupled or attached to the ultrasound generating horn of the ultrasound transducer 14. The distal end of the ultrasound transmission member 20 is coupled or attached to a distal head member 30 at the distal end of the catheter 16.

The structure and configuration of the proximal connector assembly 22 of the first embodiment may be the same as that described and shown in FIG. 10 of U.S. Pat. No. 5,267,954 (Nita), the entirety of such patent being hereby expressly incorporated herein by reference.

A fluid infusion sidearm 24 extends from proximal connector assembly 22 and is fluidly communicative with a hollow bore extending through at least a distal portion of the proximal connector assembly 22 and into an elongate hollow infusion fluid lumen 26 extending through the catheter body 18. A source 28 of pressurized or pumped liquid (e.g., 0.9% NaCl solution) is connected to the fluid infusion sidearm 24 to permit infusion of fluid through the bore of the proximal connector assembly 22 and through the elongate lumen 26 of the catheter body 18. A distal head member 30, is mounted on the distal end of the catheter body 18. Such distal head member may be of any suitable configuration, including the blunt horizontal faced configuration 30a shown in FIGS. 2–3 and the bullet-like configuration 30b shown in FIGS. 5–6. In any case, the distal head member 30 will be provided with one or more fluid outflow apertures 34a/34b which are fluidly communicative with the fluid lumen 26 of the catheter body 18 to permit irrigation fluid to flow out of the distal head 30 of the catheter 16.

In the blunt distal head embodiment 30a shown in FIGS. 2–3, the configuration of the distal head member 30 is such that there is provided a frontal portion 36 having an outer diameter substantially equal to the outer diameter of the catheter body 18, and a rear portion 38 having an outer diameter substantially equal to the inner diameter at the distal head of the catheter lumen 26 by such configuration, the rear portion 38 of the distal head member 30a may be inserted into the distal end opening of the lumen 26 of catheter body 18 and secured thereto by frictional engagement, mechanical engagement, adhesive, heat sealing or other suitable means. The outer surface of the frontal portion 36 of the distal head member 30a is thus rendered substantially continuous and in smooth transition with the outer surface of the adjacent catheter body 18. The distal head member 30a has a central fluid passageway 32a formed therein, separate and apart from the guidewire passageway 40a which extends longitudinally through the lower portion of the distal head member 30a. Such central fluid passageway 32a opens into ancillary passageways 42a, said ancillary passageways 42a terminating laterally in the multiple fluid outflow apertures 34a formed in the sides of the distal head member 30a. By such arrangement, fluid infused through the lumen 26 of the catheter body 18 will enter the central fluid passageway 32a, of the distal head member, 30a and will subsequently pass outwardly through the lateral fluid passageways 42a and out of the fluid outflow apertures 34a. This may be accomplished while a guidewire (phantom lines) remains inserted into guidewire passageway 40a, thereby substantially blocking fluid outflow through guidewire passageway 40a.

The rate of fluid outflow through outflow apertures 34a may be controlled to effect any desired degree of irrigation and/or fluidic dilation of a surrounding anatomical structure (e.g., fallopian tube, ureter, duct, blood vessel, etc. . . . ).

The alternative distal head configuration 30b shown in FIGS. 5–7 provides a distal head member 30b having a frontal portion 36b and a rear portion 38b. Said frontal portion 36b having an outer diameter substantially equal to the outer diameter of the adjacent catheter body 18. Said rear portion 38b has an outer diameter substantially equal to the inner diameter of the distal end of the catheter lumen. By such configuration, the rear portion 38b of the distal head member 30b may be inserted into the distal end of the catheter lumen and secured thereto by frictional engagement, mechanical engagement, heat sealing, chemical adhesive, or any other suitable means. When so constructed, the lateral outer surface of the distal head member 30b is continuous, and substantially flush with the adjacent outer surface of the catheter body 18, as shown. The alternative distal head member 30b shown in FIGS. 5–7 also differs from the distal head member 30a shown in FIGS. 2–4 in that the guidewire passageway 40b serves as the central fluid passageway of the distal head 30b, as well as serving as the guidewire passageway through which a guidewire may pass longitudinally through the distal head member 30b (see guidewire shown in phantom lines).

Fluid outflow passageways 42b pass fluid laterally outward from the central guidewire lumen fluid passageway 40b and lead to multiple fluid outflow apertures 34b. Thus, when the guidewire (phantom lines) has been removed or retracted so as not to block fluid entry into the guidewire passage lumen/central fluid passageway 40b, irrigation/dilation/coolant fluid may be infused through the lumen of the catheter body 18, through the guidewire passageway/central fluid passageway 40b and subsequently outward through the lateral fluid passageways 42b and lateral fluid outflow apertures 34b, as well as through the frontal guidewire passageway opening 40b. The flow rate and volume of fluid so infused may be controlled to effect any desired degree of irrigation or dilation of a surrounding anatomical structure (e.g., fallopian tube, ureter, blood vessel or other anatomical passageway).

ii. Preferred Modes of Operation of the First Embodiment

The ultrasound system 10 of the first embodiment shown in FIGS. 1–7 may be utilized for ultrasonic-treatment of various obstructive disorders of the mammalian body wherein it is desirable to effect concomitant fluid irrigation or fluid dilation of the anatomical structure whereat the distal end of the catheter 18 is positioned.

Examples of procedures wherein the ultrasound system 10 of the first embodiment may be employed include the ultrasonic ablation of atherosclerotic plaque, thrombus or other obstructive matter within the lumen(s) of mammalian blood vessel(s). Also, as described more fully in the examples set forth herebelow, the ultrasound system 10 of the first embodiment may be utilized to effect dilation and/or removal of obstructive matter (e.g., scar tissue, tumors, congenitally aberrant tissue, etc. . . . ) which obstruct tubular passageways of the body including the ducts and passageway of the urogenital tract (e.g., urethra, ureter, fallopian tubes).

EXAMPLE 1

In a first example, an ultrasound system 10 of the first embodiment of the present invention may be utilized to treat obstructions of the fallopian tubes of a female human being.

Fallopian tube obstructions are known to occur due to the formation of scar tissue within the lumens of the fallopian tubes following the occurrence of fallopian tube infections, such as chlamydia infections.

In treating such blockage of the fallopian tubes, a standard guidewire having an outer diameter of approximately 0.14.÷0.25 inch is inserted transvaginally and advanced, with radiographic and/or endoscopic guidance, into the obstructed fallopian tube to a point where the distal end of the guidewire 50 is situated adjacent the offending fallopian tube obstruction. After the guidewire has been positioned, the proximal end of the guidewire 50 is inserted into the distal guidewire passageway 40a/40b of the catheter 18 and the catheter 18 is advanced over the guidewire, using standard catheter advancement technique, to a point where the distal head 30 of the catheter 18 has been advanced to a position adjacent the obstruction to be treated. During such advancement of the catheter, the proximal end of the guidewire 50 will emerge out of the guidewire sidearm 52 of the proximal connector assembly 22 so as to render the proximal portion of the guidewire freely accessible to the operator for subsequent manipulation, extraction or exchange of the guidewire 50, if desired.

The pressurized fluid source or pump 28 is then utilized to pass a flow of irrigation/dilation fluid, such as 0.9% NaCl solution or other physiologically compatible liquid, through line 56 and into sidearm 24 of proximal end connector assembly 22. The fluid so infused will then pass, in the distal direction, through the internal bore of the proximal connector assembly 22, through the lumen 26 of catheter 18 and out of the fluid outflow apertures 34a/34b of the distal head 30 of the catheter device 16.

The flow rate of irrigation/dilation fluid out of outflow apertures 34a/34b may be adjusted and controlled so as to provide a controlled degree of a) fluid-induced dilation of the fallopian tube lumen immediately adjacent the obstruction to be treated and/or b) impingement of fluid against the obstructing scar tissue or other matter.

Thereafter, the signal generator 12 may be energized by depression of on/off foot pedal 11, thereby sending an electrical signal through line 13 to ultrasound transducer 14. Such electrical signal is converted to ultrasonic vibration by ultrasound transducer 14 and the ultrasonic vibration is passed, via proximal connector assembly 22, into the ultrasound transmission wire or member 20, thereby causing ultrasonic vibration of the distal head 30 of the catheter 16.

With continued infusion of the irrigation/dilation fluid, the catheter 16 may be advanced, or otherwise moved back and forth, such that the ultrasonic vibration of the distal head 30 of the catheter 16 will effect morcellation or reduction of the obstructive matter. Such morcellation or reduction of the obstructive matter by the ultrasonic vibration of the distal head 30 may be effected by direct contact of the vibrating distal head 30 against the obstructive matter and/or by cavitation effect created as a result of the ultrasonically vibrating distal head 30 in the fluid environment created by the controlled infusion of the infusion/dilation fluid adjacent the obstructive lesion to be treated.

In some cases, it may be desirable to initially employ a first catheter 16 having a distal head 30 designed for initial dilation of the surrounding fallopian tube lumen and impingement of the irrigation fluid against the offending lesion, and to subsequently utilize one or more additional embodiments of the catheter 16 having different designs of the distal head 30 so as to effect differing degrees of fluid impingement against the offending lesion and/or fluidic dilation of the surrounding luminal wall of the fallopian tube, during differing stages of the procedure. For example, in some procedures it may be desirable to utilize three (3) separate catheter devices 16, as follows:

| CATHETER 1 | Small size (OD = .5–1.2 mm) | Distal head having one or more fluid outflow apertures in frontal surface of tip to direct irrigation/dilation fluid into direct impingement with obstructive matter. |
|---|---|---|
| CATHETER 2 | Medium size (OD = 1.2–2.0 mm) | Distal head having fluid outflow apertures in frontal surface of tip and around the lateral sides of tip so as to simultaneously direct |

-continued

| | | |
|---|---|---|
| | | irrigation/dilation fluid in a) a forward direction so as to impinge against the obstructive matter and b) in lateral directions so as to exert external dilatory pressure against the surrounding tube wall. |
| CATHETER 3 | Large size (OD = 2.0–3.5 mm) | Distal head having no fluid outflow apertures in front surface of tip and multiple fluid outflow apertures around lateral sides of tip to exert lateral dilatory pressure against the surrounding tube only. |

In addition to effecting ultrasonic ablation or breakdown of the obstructive matter, the ultrasonic vibration of the distal head 30 of the catheter 16 may also cause relaxation of smooth muscle and resultant dilation of the fallopian tube, thereby permitting the catheter 16 to be advanced back and forth through the previously obstructed region of the fallopian tube.

In this example, it is preferable that the ultrasonic vibration of the distal catheter tip 30 be of an optimized frequency and wave form modulation to effect the desired ablation of the obstruction for inducing smooth muscle relaxation and resultant dilation of the obstructed fallopian tube.

One or more inflatable dilation balloons mounted on the ultrasound catheter device 16 or mounted on a separate balloon catheter may be utilized in conjunction with the ultrasound catheter 16, to effect dilation and opening of the obstructed region of the fallopian tube.

After the procedure has been completed and the patency of the obstructed fallopian tube restored, the catheter 16 may be extracted and removed.

EXAMPLE 2

In a second example, the ultrasound system 10 of the first embodiment of the present invention may be utilized to treat obstructions of the male urethra resulting from benign prostatic hypertrophy or other prostate enlargement.

In this example, the catheter device 16 of the first embodiment is inserted, with or without the assistance of a pre-inserted guidewire 50, into the male urethra. The catheter 16 is then advanced to a point where the distal head 30 of the catheter 16 is positioned adjacent the obstructing prostatic tissue.

A pressurized fluid source or pump 28 may be utilized to pump or otherwise expel fluid through tube 54, through sidearm 24, through the longitudinal bore of the proximal connector assembly 22, through the lumen 26 of catheter 16 and out of the distal fluid outflow apertures 34a/34b. The flow rate and quantity of the irrigation/dilation fluid being infused may be specifically adjusted and/or controlled so as to effect the desired degrees of a) impingement of the fluid against the obstruction and/or b) fluidic dilation of the surrounding anatomical structures (e.g., the urethra).

Concomitant with the infusion of the irrigation/dilation fluid, signal generator 12 may be energized by depression of on/off foot pedal 1, thereby sending an electrical signal through line 13 to ultrasound transducer 14. Ultrasound transducer 14 will convert the electrical signal to ultrasonic vibration and, via proximal connector assembly 22, will pass such ultrasound vibration through ultrasound transmission member 20 to the distal head 30 of the catheter 16. Ultrasonic vibration from the catheter tip may thereby result in a) relaxation and dilation of the smooth muscle of the urethra and/or b) ultrasonic ablation or morselling of the obstruction.

For smooth muscle relaxation the preferred ultrasound frequency is 20 kz to 1 MHz. For morselling or ablating the obstructing prostate tissue, the preferred ultrasound frequency is 20 kz to 100 MHz.

As described above in Example 1, it may also be desirable to utilize two or more separate catheters 16 having distal heads 30 of differing design, with different positions and configurations of the fluid outflow apertures 34a/34b, to facilitate optimal performance of various phases of the procedure.

After the prostatic obstruction of the urethra has been ultrasonically ablated and/or dilated so as to restore patency and urinary flow through the urethra, the catheter 16 may be extracted and removed.

The foregoing Examples 1 and 2 are intended to illustrate certain specific intended applications of the ultrasound system 10 of the first embodiment of the invention, and are not intended to provide a comprehensive discussion of all possible ablative or dilative procedures wherein the ultrasound system 10 may be employed.

iii. Elements and Components of the Second Embodiment

FIGS. 8–11 of the drawings are directed to a second embodiment of an ultrasound system 10a of the present invention. As shown, such second embodiment ultrasound system 10a generally comprises a signal generator 12a, an ultrasound transducer 14a and an elongate catheter 16a, having a proximal connector assembly 22a positioned on the proximal end thereof for coupling the catheter 16a to the ultrasound transducer 14a.

The proximal connector assembly 22a of the second embodiment ultrasound system 10a may be constructed and configured substantially the same as that described here above and in incorporated U.S. Pat. No. 5,267,954 (Nita), however it will be appreciated that in accordance with the showing of the second embodiment in FIG. 8 of this patent application such ultrasound connector assembly 22a will include an additional suction or aspiration sidearm 60 and a separate suction or aspiration tube or secondary lumen (not shown) within the hollow bore of the connector assembly 22a and which is continuous with and fluidically connected to an aspiration lumen or tube member to which extends longitudinally through the catheter body 18a for withdrawal or aspiration of debris.

The catheter 16a preferably comprises an elongate flexible catheter sheath having an ultrasound transmission member or wire 20a extending longitudinally therethrough. The proximal end of the ultrasound transmission member or wire 20a extends proximally through the proximal connector assembly 22a and is thereby coupleable or connectable to the ultrasound transducer 14a. The distal end of the ultrasound transmission member wire 20a is coupled or connected to the distal head member 30c of the catheter 16a so as to transmit ultrasonic vibration into the distal head member 30c.

The catheter 16a of the second embodiment shown in FIGS. 8–11 is a "monorail" type of catheter having a guidewire passage lumen 51 extending only through a distal portion of the catheter body 18a. In the embodiment shown, the guidewire passage lumen 51 comprises a tube which extends from the distal guidewire passage aperture 40c formed in the distal end of the distal head member 30c to a sidewall guidewire passage aperture 41a formed in the sidewall of the catheter body 18a, at a location such as that shown in FIG. 8. By such "monorail" arrangement, the proximal end of a guidewire may be passed into distal guidewire aperture 40c and advanced through guidewire lumen 51 so as to subsequently exit the catheter body 18a through sidewall aperture 41a. The proximal portion of the guidewire 50 may reside outboard of the catheter body 18a as is typical of "monorail" type catheters.

It will be appreciated that an over-the-wire embodiment may also be designed incorporating a guidewire tube or lumen which extends longitudinally through the entire catheter body 18a, with a separate guidewire passage sidearm formed in the proximal connector 22a, in a manner similar or the same as that shown in FIG. 1 with respect to the first embodiment described hereabove.

An aspiration tube member 70 extends longitudinally through the internal bore 26a of the catheter body 18a and longitudinally through a separate dedicated bore formed in the distal head member 30c as shown. The distal end of the aspiration tube member 70 is flush with the distal or frontal face of the distal head member 30c. The proximal end of the aspiration tube member 70 is fluidly connected or continuous with aspiration sidearm 60, thereby forming a continuous dedicated aspiration channel through the catheter 16a. Aspiration pump 62 is connected to aspiration sidearm 60 by way of tube 64. Debris collection vessel 66 is connected to aspiration pump 62 by tube 63. By such arrangement, aspiration pump 62 may be utilized to withdraw or aspirate debris from the area adjacent the distal end of the catheter, in a proximal direction, through aspiration tube member 70 and into debris collection vessel 66.

iv. Preferred Modes of Operation of the Second Embodiment

With reference to FIGS. 8–11, the ultrasound system 10a of the second embodiment may be operated to effect ultrasonic dilation, morselling, pulverization or other treatment of obstructive matter within a vessel or passageway of a mammalian body. Concomitant with or separate from the ultrasonic treatment, the system 10a may also be utilized to a) infuse irrigation/coolant/dilation fluid through the catheter 16a and out of the distal end thereof and b) aspirate debris, fluid or other matter, in a proximal direction, through the catheter 16a and into the debris collection vessel 66.

The aspiration and debris collection capability of the system 10a of the second embodiment is particularly useful in applications wherein it is desired to promptly remove or suction away any particles of solid matter which may be created or liberated as a result of the ultrasonic treatment process. The ability to aspirate and suction away debris or particles of solid matter is particularly important in vascular applications, wherein it is desirable to avoid any embolization or migration of solid matter into the organ or tissue, which is perfused by the blood vessel wherein the treatment is being applied. For example, in procedures wherein ultrasound is utilized to treat or ablate obstructions of the extracranial and/or intracranial blood vessels which profuse the brain, it is highly desirable to prevent the passage of any solid particulate matter into the brain, as such may result in highly undesirable sequelae such as iatrogenic stroke or embolization of smaller blood vessels which may be situated downstream from the site of the treatment procedure. In such cerebrovascular applications, the ability to promptly aspirate any solid particles which may have been created or released by the ultrasonic procedure is useful to prevent such solid particles from resulting in untoward embolization of the brain.

Arterial blood flow to the brain is provided mainly by four (4) large extracranial arteries, two common carotid arteries and two (2) vertebral arteries, which feed smaller intracranial arteries. The two (2) vertebral arteries originate from the right and left subclavian arteries, respectively, and pass into the cranium through the foramen magnum. The vertebral arteries give off branches to form the anterior spinal artery, the posterior and inferior cerebellar arteries, and the basilar artery. The common carotid arteries bifurcate into the internal and external carotid arteries. The internal carotid arteries pass into the cranium and give off the ophthalmic, posterior communicating and anterior choroidal arteries. The internal carotid arteries also form, by terminal bifurcation, the anterior and middle cerebral arteries.

Obstructions may form in any of the intracranial or extracranial cerebral arteries, including all of those described hereabove. Such obstructions may result from atherosclerotic narrowing of those arteries, or may come about due to a thromboembolic event, such as the migration of a blood clot into the cerebral circulation from the heart or some other location.

The clinical significance and severity of symptoms resulting from obstruction of the cerebral blood vessels may vary, depending on the origin or type of obstruction, the location of the obstruction and other factors. The degrees of resultant ischemia may vary, ranging from a) a "transient ischemic attack" (TIA) wherein a transient focal loss of neurologic function occurs, to b) a "partial non-progressing stroke" (PNS) producing minor persistent neurologic disability to c) a "completed stroke" (CS) producing major permanent neurologic disability.

The following are examples of applications wherein the ultrasound system 10a of the second embodiment of the present invention is utilized to treat obstructions of the cerebral blood vessels so as to treat or prevent conditions such as TIA, PNS or CS as described hereabove.

EXAMPLE 3

In this example, the second embodiment of the ultrasound system 10a shown in FIGS. 8–11 is utilized to treat an atherosclerotic obstruction of the extracranial internal carotid artery of a human being.

Initially, a guidewire 50 is percutaneously inserted into a peripheral artery and advanced, under radiologic guidance, to a position whereat the distal end of the guidewire 50 is positioned in the internal carotid artery immediately upstream of the obstruction to be treated.

The proximal end of the guidewire is passed into the distal guidewire aperture 40c of the catheter device 16a and the catheter device 16a is advanced over the guidewire, with the proximal end of the guidewire 50 emerging from the sidewall guidewire aperture 41a as the catheter 16a is further advanced to a point where the distal head 30c of the catheter 16a is positioned adjacent the obstruction to be treated.

The guidewire 50 is then fully or partially withdrawn into the tubular guidewire lumen 51 of the catheter device 16a.

Foot pedal 11a is depressed to energize signal generator 12a such that an electrical signal emitted by signal generator 12a passes through line 13a to ultrasound transducer 14a. Ultrasound from ultrasound transducer 14a passes, via proximal connector assembly 22a, into the proximal end of the ultrasound transmission member 20a and travels through ultrasound transmission member 20a to distal head member 30c, thereby causing ultrasonic vibration of distal head member 30c.

Concomitant with the delivery of ultrasound to the distal head member 30c, a flow of 0.9% Nacl solution is pumped via pump 28a, through the catheter lumen 26a. Such flow of saline solution through the catheter lumen 26a accomplishes the dual function of a) bathing and cooling the ultrasound transmission member 20a to prevent excessive heat build-up as a result of the ultrasonic vibration thereof and b) providing a flow of irrigation/dilation fluid into central fluid passageway 32c, through secondary fluid passageway 42c and out of fluid outflow apertures 34c.

Also, concomitant with the delivery of ultrasound to the distal head 30c and the infusion of irrigation/dilation fluid out of fluid outflow apertures 34c, a suction is applied, via suction pump 62, through line 64 to aspiration sidearm 60, thereby drawing negative pressure on the lumen of aspiration tube 70 so as to draw particulate matter or other debris adjacent the distal tip of the catheter 16a into the distal aspiration port 72, through aspiration tube 70 and into debris collection vessel 66.

The flow of saline solution out of the fluid outflow apertures 34c and the intake of matter into aspiration port 72 may be adjusted and controlled, by adjustment and control of infusion pump 28a and aspiration pump 62, such that the two (2) flow rates are substantially equal to one another, such that saline solution flowing out of the fluid outflow apertures 34c will circulate adjacent the distal head member and be subsequently withdrawn into the aspiration port 72 and through aspiration tube 70 into debris container 66. By such equilibration of the infusion outflow and aspiration outflow rate, a continuous fluid turnover may be affected to accomplish prompt lavage and removal of any particulate matter or other debris generated adjacent the distal head 30c of the catheter device 16a.

The catheter 16a may be proximally advanced and/or moved back and forth so as to effectively treat the obstructive lesion, thereby improving blood flow and restoring patency to the lumen of the internal carotid artery wherein the treatment is applied.

When desired, the aspiration pump 62 may be turned off and a quantity of radiographic contrast medium may be passed into infusion sidearm 58, through catheter lumen 26a and out of distal fluid outflow apertures 34c to radiographically visualize the area of the obstruction for purposes of determining whether the treatment has effectively ablated or opened the obstruction.

After successful treatment and opening of the obstruction has been radiographically verified, the catheter device 16a may be withdrawn and removed.

EXAMPLE 4

In this example, the second embodiment of the ultrasound system 10a shown in FIGS. 8–11 is utilized to ultrasonically treat an obstruction of the intracranial middle cerebral artery of a human being.

Initially, a guidewire 50 is percutaneously inserted into a peripheral artery and advanced, under radiographic guidance, to a position whereat the distal end of the guidewire 50 is positioned within the cerebral artery, immediately upflow of the obstruction to be treated.

Thereafter, the proximal end of the guidewire 50 is inserted into the guidewire entry aperture 40c in the distal head 30c of the catheter device 16a and the catheter device 16a is advanced in the proximal direction, with the proximal end of the guidewire 50 emerging outwardly through sidewall guidewire aperture 41a. The advancement of the catheter 16a is continued until the distal head 30c is positioned in the middle cerebral artery immediately adjacent the obstruction to be treated.

Thereafter, the guidewire 50 is fully or partially withdrawn, at least to a point whereat the distal tip of the guidewire is within the lumen 26a of the body of catheter 16a.

Foot pedal 11a is depressed to energize signal generator 12a, thereby sending an electrical signal through line 13a to ultrasound transducer 14a. Ultrasound from transducer 14a passes, via proximal connector assembly 22a, into ultrasound transmission member 20a and is carried by said ultrasound transmission member 20a to the distal head 30c of the catheter device 16a, thereby causing the distal head 30c to vibrate ultrasonically within the desired frequency range.

Relaxation of the vascular smooth muscle within the middle cerebral artery results from the ultrasonic vibration within the above-stated frequency range, thereby causing some dilation of the middle cerebral artery in the region of the obstruction to be treated.

Concomitant with the delivery of ultrasound to the distal head member 30c, a flow of 0.9% NaCl solution is pumped via pump 28a, through the catheter lumen 26a. Such flow of saline solution through the catheter lumen 26a accomplishes the dual function of a) bathing and cooling the ultrasound transmission member 20a to prevent excessive heat build-up as a result of the ultrasonic vibration thereof and b) providing a flow of irrigation/dilation fluid into central fluid passageway 32c, through secondary fluid passageway 42c and out of fluid outflow apertures 34c.

Also, concomitant with the delivery of ultrasound to the distal head 30c and the infusion of irrigation/dilation fluid out of fluid outflow apertures 34c, a suction is applied, via suction pump 62, through line 64 to aspiration sidearm 60, thereby drawing negative pressure on the lumen of aspiration tube 70 so as to draw particulate matter or other debris adjacent the distal tip of the catheter 16a into the distal aspiration port 72, through aspiration tube 70 and into debris collection vessel 66.

The flow of saline solution out of the fluid outflow apertures 34c and the intake of matter into aspiration port 72 may be adjusted and controlled, by adjustment and control of infusion pump 28a and aspiration pump 62, such that the two (2) flow rates are substantially equal to one another, such that saline solution flowing out of the fluid outflow apertures 34c will circulate adjacent the distal head member and be subsequently withdrawn into the aspiration port 72 and through aspiration tube 70 into debris container 66. By such equilibration of the infusion outflow and aspiration outflow rate, a continuous fluid turnover may be affected to accomplish prompt lavage and removal of any particulate matter or other debris generated adjacent the distal head 30c of the catheter device 16a.

The catheter 16a may be proximally advanced and/or moved back and forth so as to effectively treat the obstructive lesion, thereby improving blood flow and restoring patency to the lumen of the internal carotid artery wherein the treatment is applied.

When desired, the aspiration pump 62 may be turned off and a quantity of radiographic contrast medium may be passed into infusion sidearm 58, through catheter lumen 26a and out of distal fluid outflow apertures 34c to radiographically visualize the area of the obstruction for purposes of determining whether the treatment has effectively ablated or opened the obstruction.

After successful treatment and opening of the obstruction has been radiographically verified, the catheter device 16a may be withdrawn and removed.

It will be appreciated that the foregoing drawings, descriptions of preferred embodiments, and examples serve to describe and illustrate specific embodiments of the invention but do not describe or encompass every possible embodiment of the invention which may be constructed or utilized. Accordingly, it is intended that the above-set-forth description, drawings and examples be broadly construed so as to encompass all foreseeable additions, modifications and alterations which those of skill in the art would be inclined to make.

What is claimed is:

1. A method of ultrasonically treating an obstruction of a blood vessel, said method comprising the steps of:
   a) providing an ultrasound catheter having a proximal end and a distal end, said catheter comprising:
      i) an elongate flexible catheter having a proximal end, a distal end and a longitudinal axis extending longitudinally therethrough;
      ii) at least one ultrasound transmission member extending longitudinally through said catheter body and coupleable to an ultrasound source, said ultrasound transmission member having a distal end which is substantially coterminous with the distal end of said catheter body;
      iii) at least one fluid infusion lumen extending longitudinally through said catheter body and opening through at least one fluid outflow aperture formed at the distal end of said catheter body;
      iv) at least one aspiration lumen extending longitudinally through said catheter body and opening through at least one aspiration port formed in the distal most centimeter of said catheter body;
   b) inserting said catheter device, distal end first, into the vasculature and advancing said catheter to a point where the distal end of said catheter is adjacent the obstruction to be treated;
   c) coupling said ultrasound transmission member to an ultrasound source and utilizing said ultrasound source to pass ultrasound through said ultrasound transmission member to the distal end of said catheter;
   d) infusing a liquid infusate through said infusion lumen in contact with said ultrasound transmission member and out of said distal outflow aperture, thereby removing excess heat from said ultrasound transmission member;
   e) applying suction to said aspiration lumen to draw matter into said distal aspiration port and through said aspiration lumen of said catheter.

2. The method of claim 1 utilized to treat a cerebral vascular obstruction, wherein step b) of said method further comprises:
   inserting said catheter, distal end first, into the vasculature and
   advancing said catheter to a point where the distal end of said catheter is positioned in an intracranial or extracranial cerebral blood vessel, adjacent the obstruction to be treated.

3. The method of claim 2 wherein the obstruction to be treated is in a carotid artery and wherein the distal head of said catheter is positioned within said carotid artery adjacent the obstruction to be treated.

4. The method of claim 2 wherein the obstruction to be treated is in a vertebral artery and wherein step b) further comprises positioning the distal end of said catheter within said vertebral artery adjacent the obstruction to be treated.

5. The method of claim 2 wherein the obstruction to be treated is in a basilar artery and wherein step b) further comprises positioning the distal end of said catheter within said basilar artery adjacent the obstruction to be treated.

6. The method of claim 2 wherein the obstruction to be treated is in a anterior cerebral artery and wherein step b) further comprises positioning the distal end of said catheter within said anterior cerebral artery adjacent the obstruction to be treated.

7. The method of claim 2 wherein the obstruction to be treated is in a middle cerebral artery and wherein step b) further comprises positioning the distal end of said catheter within said middle cerebral artery adjacent the obstruction to be treated.

8. The method of claim 2 wherein the obstruction to be treated is in a posterior cerebral artery and wherein step b) further comprises positioning the distal end of said catheter within said posterior cerebral artery adjacent the obstruction to be treated.

9. The method of claim 2 wherein said method further comprises the step of:
   maintaining the rate of infusion through said infusion lumen and
   maintaining the rate of aspiration through said aspiration lumen such that said rates of infusion and aspiration are substantially equivalent.

10. The method of claim 1 wherein step c) further comprises:
    utilizing said ultrasound source to pass ultrasound within the frequency range of 20 kHz to 1 MHz through said ultrasound transmission member to the distal end of said catheter to thereby cause ultrasound induced smooth muscle relaxation and resultant dilation of the anatomical passageway.

* * * * *

UNITED STATES PATENT AND TRADEMARK OFFICE
CERTIFICATE OF CORRECTION

PATENT NO. : 6,929,632 B2
DATED : August 16, 2005
INVENTOR(S) : Nita et al.

It is certified that error appears in the above-identified patent and that said Letters Patent is hereby corrected as shown below:

Title page,
Item [75], Inventors, delete "Vieyo" and insert -- Viejo --; and delete "Corona Del Mar" and insert -- Newport Beach --.

Column 2,
Line 32, after "treatment process" insert -- . --.

Column 7,
Line 63, delete "foot pedal 1" and insert -- foot pedal 11 --.

Column 14,
Line 21, delete "a anterior" and insert -- an anterior --.

Signed and Sealed this

Third Day of January, 2006

JON W. DUDAS
*Director of the United States Patent and Trademark Office*